United States Patent [19]

van Andel

[11] Patent Number: Plant 7,611

[45] Date of Patent: Jul. 30, 1991

[54] ALSTROEMERIA NAMED STAPURZUL

[75] Inventor: Jacob van Andel, Aalsmeer, Netherlands

[73] Assignee: Van Staaveren B.V., Netherlands

[21] Appl. No.: 520,353

[22] Filed: May 7, 1990

[51] Int. Cl.[5] ..... A01H 5/00

[52] U.S. Cl. ..... Plt./68

[58] Field of Search ..... Plt./68

*Primary Examiner*—James R. Feyrer

*Attorney, Agent, or Firm*—Charles W. Rummler

[57] ABSTRACT

A new Alstroemeria characterized by its medium sized blooms, the outer petals of which are distinguished by a generally violet purple coloration and having short parallel streaks of a purplish color extending from the central portion of the petal to its outer margin, the outer petals being generally of a cuneate shape. The inner petals are of a generally ovate shape with an aristate tip and generally of a violet purple color with a white mid-portion and covered from end-to-end with short deep purple pencil stripes. This plant is further distinguished by its strong vigorous and upright growth habit with the main stem reaching a height of about 180 cm and bearing a raceme of many flowers which are produced profusely and continuously from Spring to mid-season.

1 Drawing Sheet

BACKGROUND OF THE NEW PLANT

This new Alstroemeria variety originated as a seedling of a hybrid resulting from my crossing of plants selected from individually identified members of my breeding stock maintained in my nursery at Aalsmeer, The Netherlands, for breeding purposes, this particular seedling having been selected by me for propagation and tests because of its relatively large flowers of a generally violet purple coloration which were produced profusely on strong upright stems appearing in a generally umble formation. This selected seedling was propagated under my direction by means of rhizomes with such satisfactory results that further propagation of this plant was done by dividing rhizomes of several successive generations which demonstrated clearly that the novel and distinctive characteristics of this seedling would hold true from generation to generation and appear to be firmly fixed.

DESCRIPTION OF THE DRAWING

My new Alstroemeria variety is illustrated by the accompanying photographic drawing which, in full color, shows fully developed blossoms which demonstrate the unique and distinctive coloration and form of the flower, the colors being as nearly true as possible to that herein specific as can be obtained by conventional photographic procedures.

DESCRIPTION OF THE NEW PLANT

The following is a detail description of my new Alstroemeria variety as observed at Aalsmeer, Holland, with the color designations being according to the R.H.S. Colour Chart of The Royal Horticultural Society of London, England.

THE PLANT

Origin: Seedling.

Parentage:

*Seed parent.*—Variety number 1016-1 (Unnamed and unpatented).

*Pollen parent.*—Variety 1272-1 (Unnamed and unpatented).

Classification:

*Botanic.*—Alstroemeria Hybrid.

*Commercial.*—Alstroemeria.

Form: Upright bush.

Height: About 180 cm.

Flowering stem length: About 180 cm.

Growth: Strong, vigorous and upright.

Foliage:

*Quantity.*—Abundant.

*Number of leaves.*—Average, varying with the season.

*Size of leaf.*—Large.

*Leaf shape.*—Generally elliptic with entire margins.

*Texture.*—Leathery.

*Color.*—Upper side — Green.

*Aspect.*—Glossy.

Rhizomes:

*Size.*—Varying with the age of the plant.

*Color.*—White.

THE BUD

Form: Pear shaped.

Diameter: About 1.5 to 2.0 cm.

Length: About 4 cm.

Rate of opening: Normal.

Color of petals:

*When sepals divide.*—Lylac purple 70 B.

*When petals begin to unfurl.*—Violet purple 77 B.

Peduncle:

*Length.*—About 2.3 cm.

*Character.*—Strong and erect.

*Color.*—Green.

THE FLOWER

Blooming habit: Continuous and profusely from Spring through Fall in greenhouse.

Size of bloom: Large.

*Diameter.*—About 6.5 cm.

*Depth.*—About 6 cm.

Borne: Singly and relatively short strong stems clustered in raceme arrangement at the upper end portion of the main stem.

Shape: When bloom matures, funnel like with petal tips curling outwardly.

Petalage:

*Number of petals.*—6.

*Arrangement.*—Generally hexagonal with two concentric circles of 3 each.

*Texture.*—Leathery.

*Color.*—Outer petals — body, 77B; base and reverse side violet purple, 77D. Inside petals — generally violet purple 77B with white mid-section 55D and with the entire petal body being covered end-to-end with short deep purple longitudinal pencil stripes.

Persistence: The flowers hang on and dry.

Fragrance: None.

Lasting quality: On the plant, about 3 weeks. As a cut flower, about 2 weeks.

THE REPRODUCTIVE ORGANS

Stamens:

*Number.*—Six.

*Arrangement.*—One opposite each petal.

*Anthers.*—Size: About 7 mm. Color: Green/Yellow.

*Filaments.*—Length: About 4 cm. Color: Light purple.

*Pollen.*—Color: Blue.

Pistils:

*Number.13* One.

Style:

*Length.*—About 4 cm.

*Color.*—Light purple.

*Stigma.*—Color: Violet.

FRUIT

Fertility: The fruit is fertile.

Color at maturity: Light Brown.

Size: Normal for genus Alstroemeria.

I claim:

1. A new and distinctive Alstroemeria plant, substantially as herein shown and described, characterized by large blossoms of an overall violet purple coloration, the outer petals being of a generally ovate-cuneate form and hexagonal arrangement, the inner petals being of a long ovate form with the upper pair substantially parallel with each other and extending in a radially opposite direction than the third petal of the inner petal group, each having a white central body portion and covered from end to end with numerous dark longitudinal purple pencil stripes.

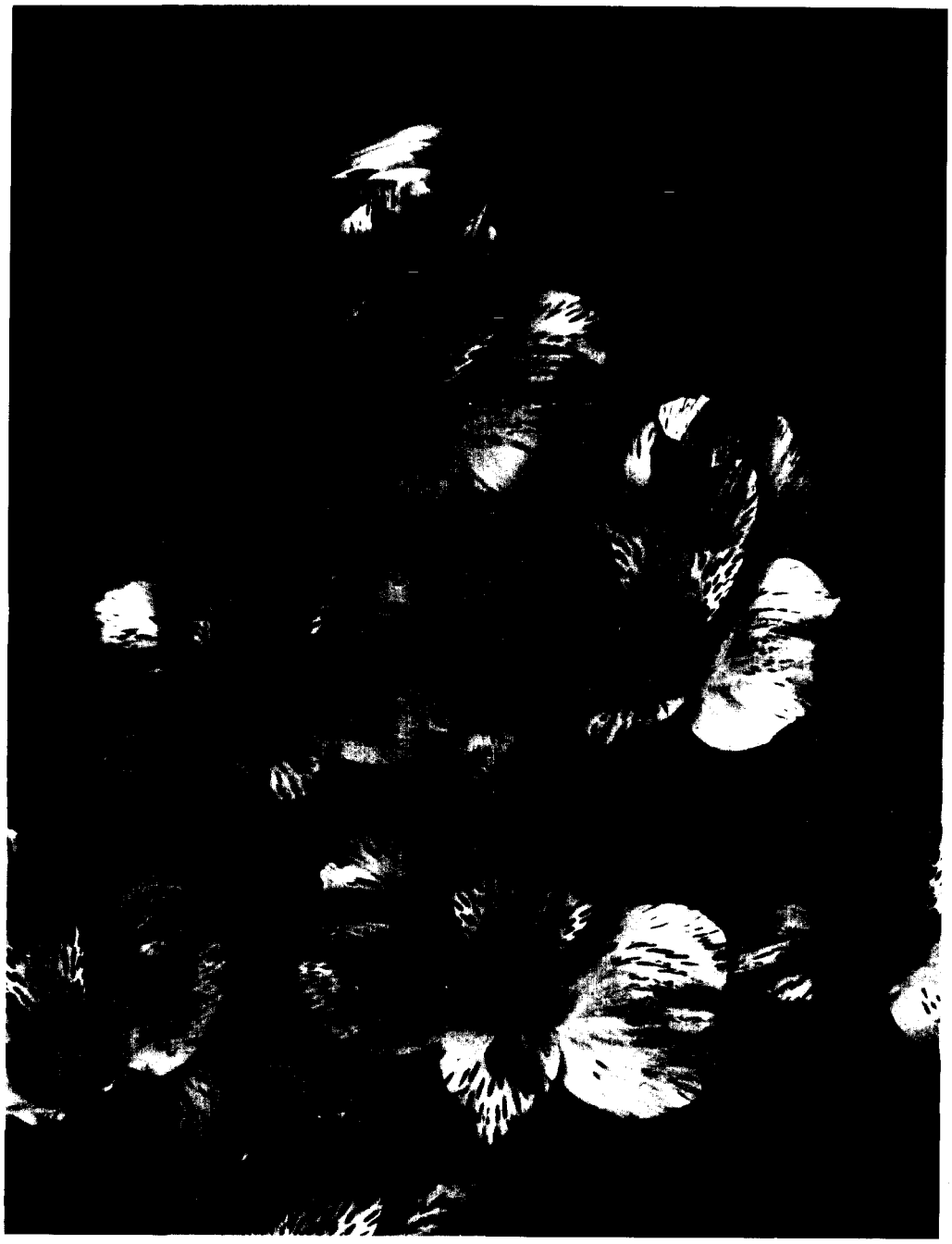

* * * * *